(12) United States Patent
Brodowski

(10) Patent No.: US 8,663,336 B1
(45) Date of Patent: Mar. 4, 2014

(54) ADJUST AND LOCK ARTIFICIAL HIP CUP

(76) Inventor: John Brodowski, Smithtown, NY (US)

( * ) Notice: Subject to any disclaimer, the term of this patent is extended or adjusted under 35 U.S.C. 154(b) by 42 days.

(21) Appl. No.: 13/573,196

(22) Filed: Aug. 30, 2012

(51) Int. Cl.
*A61F 2/32* (2006.01)

(52) U.S. Cl.
USPC .............. 623/22.23; 623/22.2; 623/22.21; 623/22.22; 623/22.29; 623/22.35; 623/22.24; 623/22.25; 623/22.26; 623/22.27; 623/22.28; 623/22.3; 623/22.31; 623/22.32; 623/22.34

(58) Field of Classification Search
USPC .......................................... 623/22.11–22.35
See application file for complete search history.

(56) References Cited

U.S. PATENT DOCUMENTS

| 4,619,658 | A | * | 10/1986 | Pappas et al. | 623/22.19 |
| 4,695,282 | A | * | 9/1987 | Forte et al. | 623/22.29 |
| 5,725,591 | A | * | 3/1998 | DeCarlo et al. | 623/22.29 |
| 5,989,293 | A | * | 11/1999 | Cook et al. | 623/22.29 |
| 6,537,321 | B1 | * | 3/2003 | Horber | 623/22.22 |

* cited by examiner

*Primary Examiner* — Thomas J Sweet
*Assistant Examiner* — Krutanjali M Shah

(57) ABSTRACT

An artificial hip cup design having an external groove for accepting a split ring or segmented split rings with knife shaped edges and specially designed set screws which expand the split ring's outer diameter. After the cup is placed in the socket of the pelvic bone, it can be readjusted, if necessary, and then locked in final position.

1 Claim, 6 Drawing Sheets

SECTION X-X

SECTION X-X

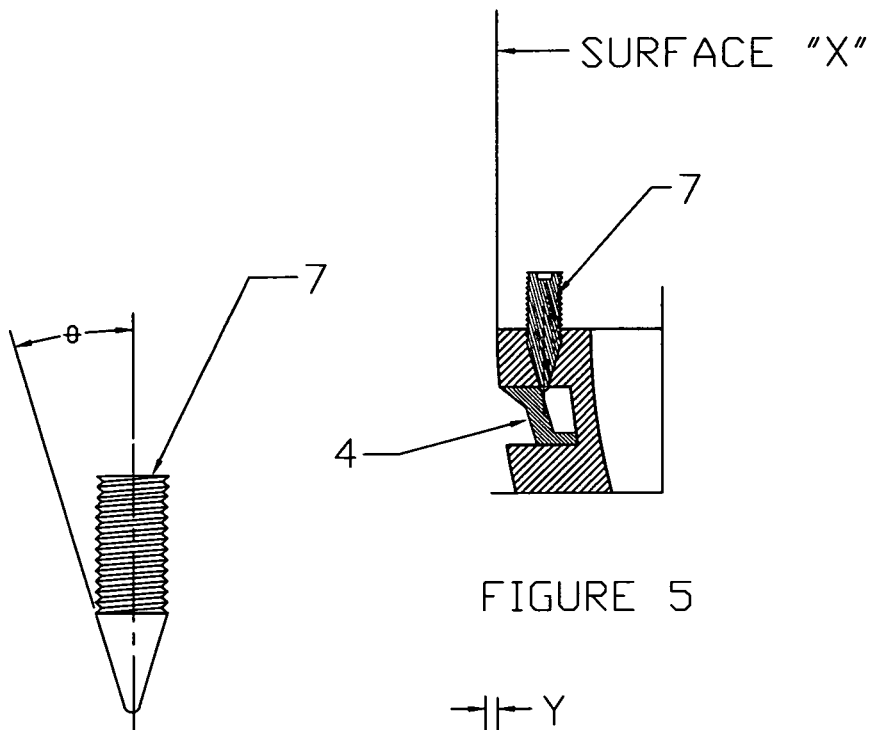
FIGURE 5
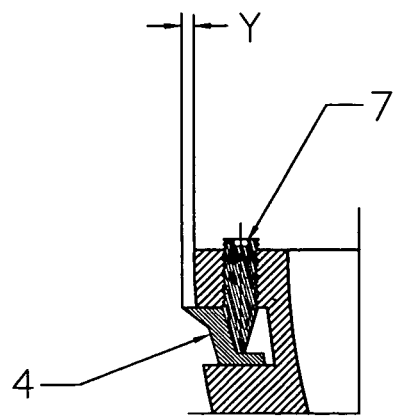
FIGURE 4
FIGURE 6

ADJUST AND LOCK ARTIFICIAL HIP CUP

BACKGROUND OF THE INVENTION

1. Field of the Invention

The present invention relates to artificial hip cup assemblies, particularly to the fixation of the cup to the pelvic bone.

2. Description of Prior Art

Various kinds of prior art artificial hip cups have been proposed and developed.

| U.S. Pat. No. 6,520,995 | March 2003 | Church |
| U.S. Pat. No. 6,709,462 | March 2004 | Hanssen |
| U.S. Pat. No. 6,712,857 | March 2004 | Roger |

The fundamental problem with the prior art cup devices is the lack of capability of adjustment of the cup to the proper position, if necessary, after it is placed in the socket in the pelvic bone. Some prior art cup devices require large force for placing them in the socket of the pelvic bone. This large force may distort the cup, albeit minutely, but this small cup distortion may eventually contribute to failure of the artificial hip device.

BRIEF SUMMARY OF THE INVENTION

An artificial hip cup is proposed with an external grove for accepting a split ring or split ring segments having knife edges. The single split ring's or split ring's segments' outside diameter is expanded by the set screws which are strategically located on the flat surface of the hip cup. After the single split ring or split ring segments are fully expanded by the set screws, the knife edges are firmly locked in the pelvic bone. Before the cup is locked in the final position, it can be adjusted easily if required.

DETAILED DESCRIPTION OF THE INVENTION

Figure 1:
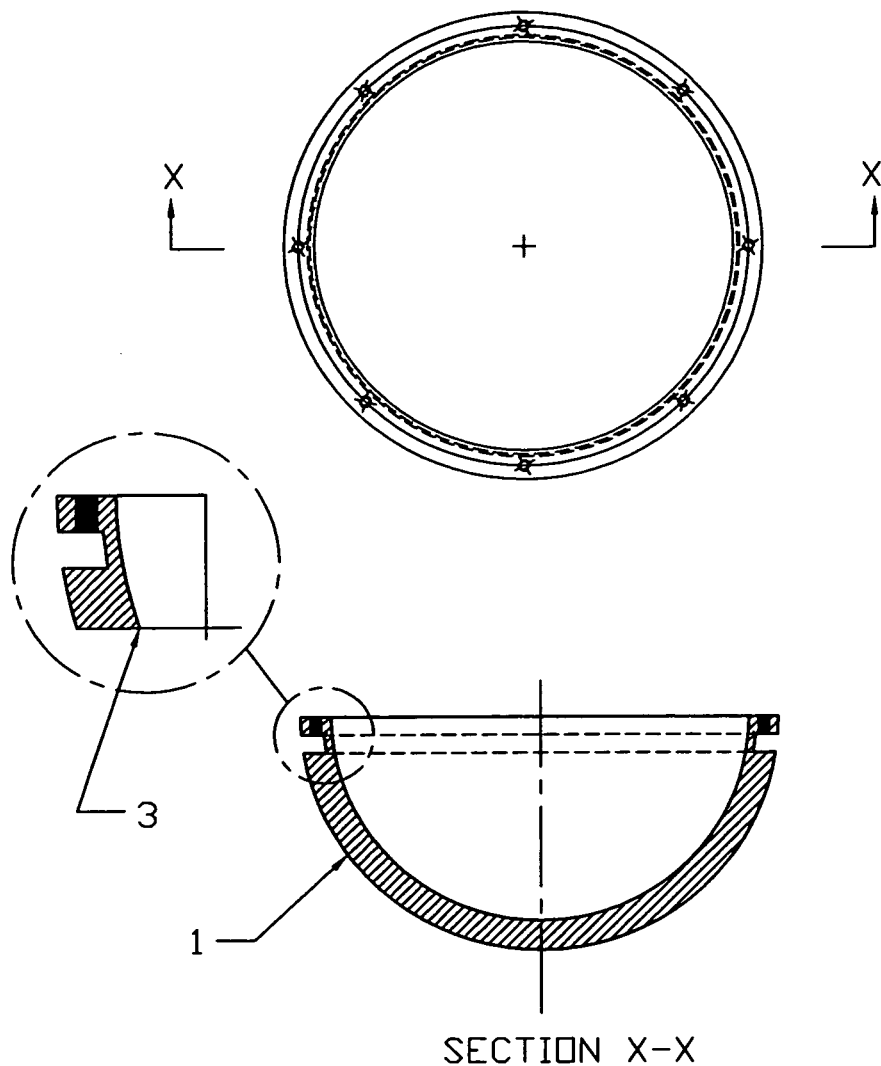
FIG. 1 Top view and cross section of the cup.
Figure 2:
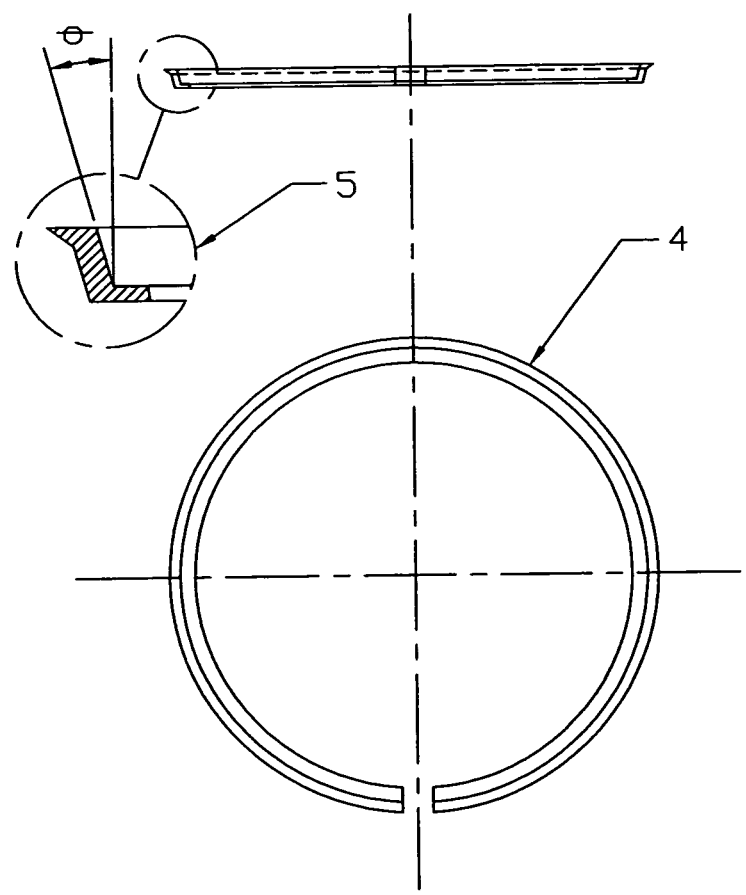
FIG. 2 Split ring
FIG. 3 Assembly of the cup
FIG. 4 Set screw
FIG. 5 Cross sectional view when ring is not expanded
FIG. 6 Cross sectional view when ring is fully expanded
FIG. 7 Split ring segments
FIG. 8 Circular ring for retaining split ring's segments

The device consists of a cup 1, FIG. 1; split ring 4, FIG. 2; and a set screw 7, FIG. 4.

FIG. 1 shows the top view of the cup with enlarged cross sectional view of the groove 3.

Figure 3:
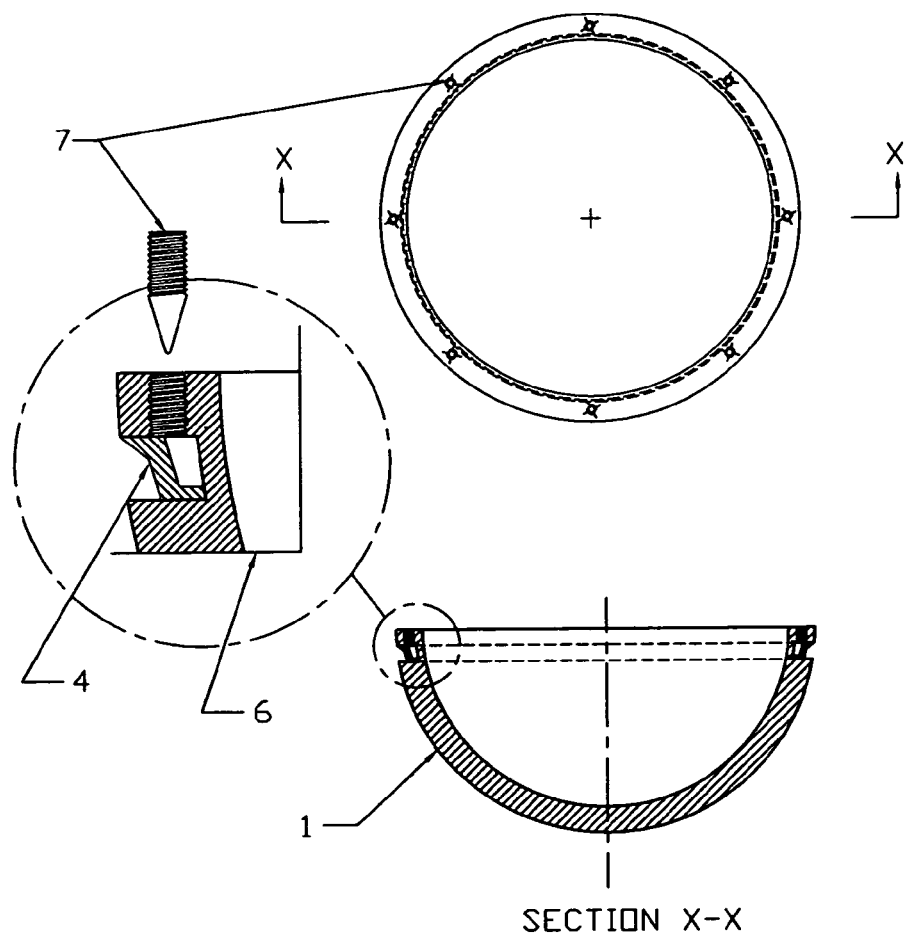

FIG. 3 shows split ring 4 inserted into the groove in the cup 1 and enlarged cross sectional view 6 of the split ring 4 nestled in the cup's groove before its diameter is expanded with set screws 7.

FIG. 5 shows set screw fully retracted and the split ring's diameter fully contracted.

When split ring 4 is fully contracted, its knife edge must not protrude beyond surface "x" of the cup 1 on FIG. 5. FIG. 6 is shows split ring's diameter fully expanded. When the split ring 4 is fully expanded, its knife edge protrudes beyond surface "x" of the cup to dimension "y".

The size of the dimension "y" will determine the quality of locking of the cup to the pelvic bone. The conical angle 0 of the set screw 7 on FIG. 4 must be equal to the angle 0 of the split ring 4 on FIG. 2.

Figure 3A:
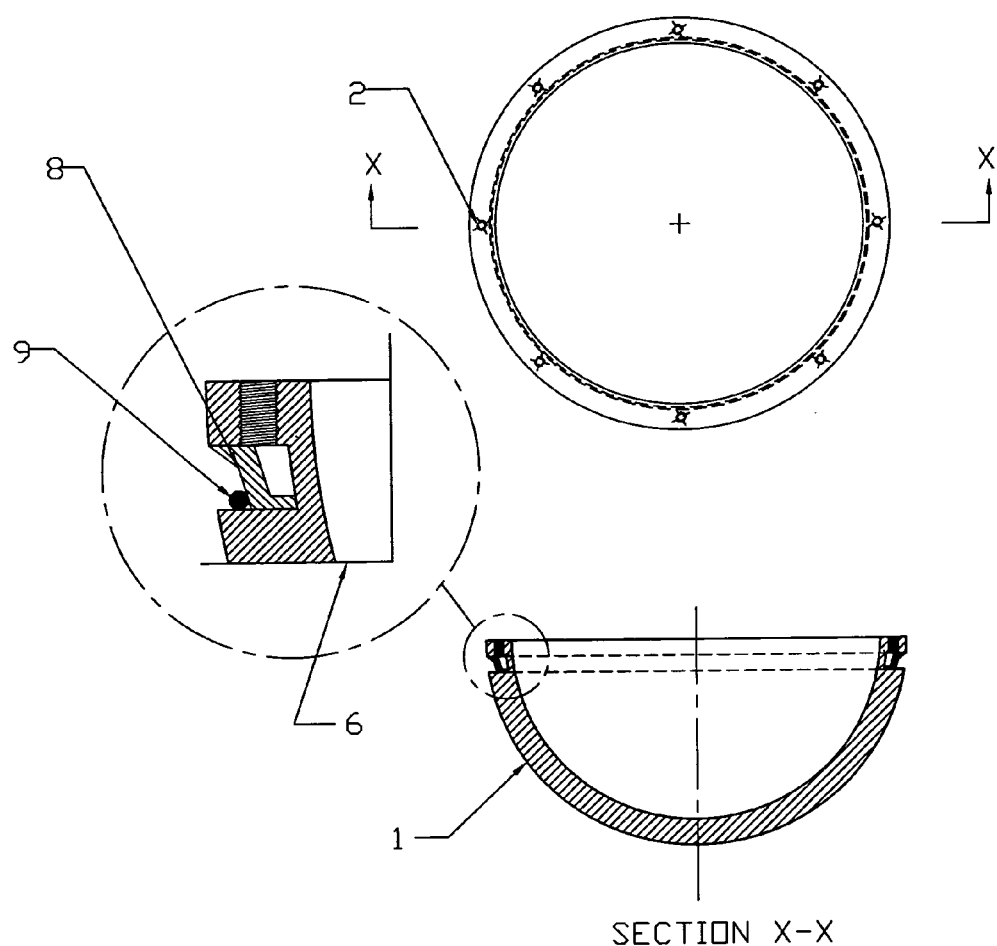

Variation of the device is shown on FIG. 3A.

Figure 7:
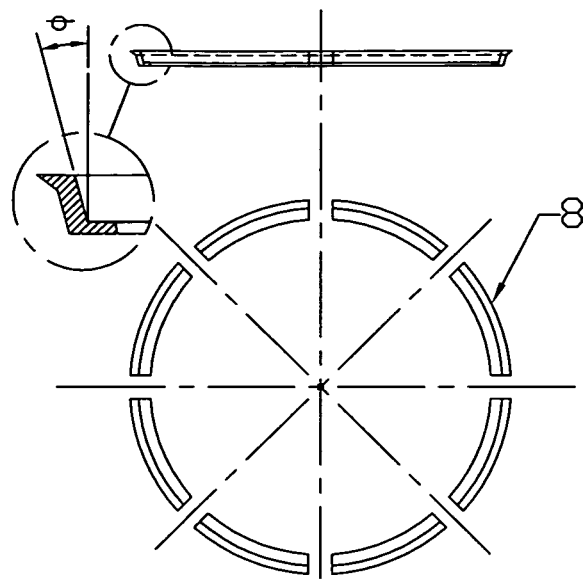
Figure 8:
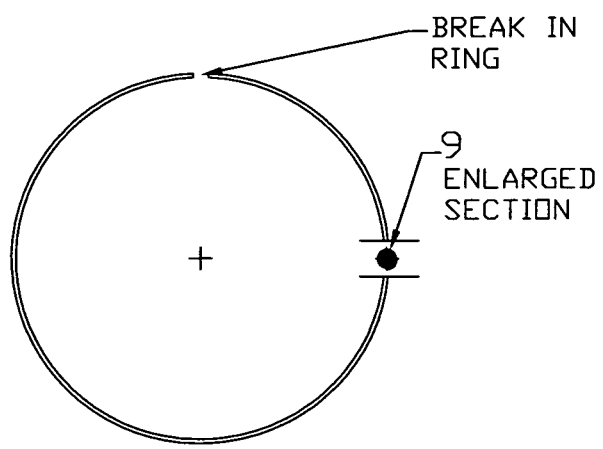

This device comprises of segmented split ring 8, FIG. 7, and circular retaining ring 9, FIG. 8. While retaining ring 9 keeps segments in place, it also allows them to expand when screws 7, FIG. 4, are turned clockwise. Similar functionality exists between the two versions of split ring 2, FIG. 2, and split ring 8, FIG. 7.

After the cup is placed in the pelvic bone, the cup assembly can be adjusted to the desired position and then locked permanently in place.

Some prior art cup designs require large force to place the cup in the pelvic bone; some are glued or screwed in place and thus deprive the surgeon of ability to make final cup adjustment if necessary.

What is claimed:

1. (a) An assembly of elements forming a cup of a type used in artificial hips with means for readjustment in the socket of the pelvic bone and with positive locking when placed in a final position, comprising: a concave spherical surface for accepting a ball of an artificial hip; an external convex surface which will be affixed to the pelvic bone, said external convex surface having circumferential groove for accepting a single split ring; an external equatorial planar surface having orthogonal multiple tapped holes for accepting set screws, said tapped holes penetrating entire thickness of a lip formed by the groove in the convex surface and planar surface of the cup, (b) A split circumferential ring having an internal angularly shaped surface and an external Surface shaped in a form of a knife edge, said ring's cross sectional footprint is identical to a cross sectional footprint of the groove in the convex external surface of the cup, and when split ring is inserted into the groove, no portion of it shall protrude beyond the external surface of the cup, (c) A set screw having one end conically shaped, said conical shape of the set screw having an angle compatible with an internal surface of the split ring, (d) A split ring, further having a variety of knife edges and identical shape but comprising of multiple segments, (e) A circularly shaped ring having a circular cross section which provides means of retaining split ring segments in said hip cup.

* * * * *